(12) United States Patent
Eichmann et al.

(10) Patent No.: US 12,111,306 B2
(45) Date of Patent: Oct. 8, 2024

(54) METHODS OF GEOLOGIC SAMPLE ANALYSIS

(71) Applicant: Saudi Arabian Oil Company, Dhahran (SA)

(72) Inventors: Shannon L. Eichmann, Houston, TX (US); Tiffany Dawn McAlpin, Richmond, TX (US)

(73) Assignee: Saudi Arabian Oil Company, Dhahran (SA)

( * ) Notice: Subject to any disclaimer, the term of this patent is extended or adjusted under 35 U.S.C. 154(b) by 122 days.

(21) Appl. No.: 17/958,809

(22) Filed: Oct. 3, 2022

(65) Prior Publication Data

US 2024/0110905 A1   Apr. 4, 2024

(51) Int. Cl.
| | | |
|---|---|---|
| *G01N 33/24* | (2006.01) | |
| *G01N 21/33* | (2006.01) | |
| *G01N 21/35* | (2014.01) | |
| *G01N 21/64* | (2006.01) | |
| *G06V 10/143* | (2022.01) | |
| *G06V 10/50* | (2022.01) | |
| *G06V 10/75* | (2022.01) | |
| *H04N 9/67* | (2023.01) | |
| *H04N 23/11* | (2023.01) | |

(52) U.S. Cl.
CPC .......... *G01N 33/241* (2013.01); *G01N 21/33* (2013.01); *G01N 21/35* (2013.01); *G01N 21/64* (2013.01); *G06V 10/143* (2022.01); *G06V 10/507* (2022.01); *G06V 10/75* (2022.01); *H04N 9/67* (2013.01); *H04N 23/11* (2023.01)

(58) Field of Classification Search
CPC ...... G01N 33/241; G01N 21/33; G01N 21/35; G01N 21/64; G01N 1/34; G01N 21/31; G01N 2021/1765; G01N 21/6456; G06V 10/143; G06V 10/507; G06V 10/75; G06V 20/80; H04N 9/67; H04N 23/11
See application file for complete search history.

(56) References Cited

U.S. PATENT DOCUMENTS

| | | | |
|---|---|---|---|
| 9,885,804 B2 | 2/2018 | Ly | |
| 2015/0284811 A1* | 10/2015 | Knight | G16B 20/00 |
| | | | 506/8 |
| 2019/0261947 A1* | 8/2019 | Themelis | A61B 5/0071 |
| 2020/0300700 A1* | 9/2020 | Hansen | G01J 3/2823 |
| 2022/0270245 A1* | 8/2022 | Ishikawa | G06T 7/0012 |
| 2023/0219118 A1* | 7/2023 | Godbole | B08B 3/10 |
| | | | 134/18 |

FOREIGN PATENT DOCUMENTS

WO     2012128764 A1    9/2012

* cited by examiner

*Primary Examiner* — Michael E Teitelbaum
(74) *Attorney, Agent, or Firm* — DINSMORE & SHOHL LLP

(57) ABSTRACT

A method of analyzing a geologic sample includes illuminating the geologic sample with a light beam and capturing an image of the geologic sample on a hyperspectral camera as a greyscale image, R-G-B color space image, or both, thereby collecting spectra having mid-wave infrared wavelengths or ultraviolet wavelengths reflected from a surface of the geologic sample. The method further includes processing the image to transform the image from the R-G-B color space, greyscale image, or both, and analyzing the Intensity to determine mineralogy, organic content, hydrocarbon presence, or combinations thereof of the geologic sample.

20 Claims, 11 Drawing Sheets

METHODS OF GEOLOGIC SAMPLE ANALYSIS

TECHNICAL FIELD

The present specification generally relates to systems and methods for measuring mineralogy, organic content, hydrocarbon presence, or combinations thereof of a geologic sample.

BACKGROUND

Extracting subsurface fuel sources may require drilling a hole from the surface to the subsurface geological formation housing the fuel. Specialized drilling techniques and materials are utilized to form a wellbore and extract the fuels. A wellbore is a hole that extends from the surface to a location below the surface to permit access to hydrocarbon-bearing subsurface formations. During drilling, samples (which may be cuttings, cores, core plugs, slabbed core, or combinations of these), are collected at the rig site and used for preliminary evaluation of reservoir rock quality and hydrocarbon presence. Well site geologists may manually assess hundreds to thousands of samples per well in order to generate qualitative descriptions and drilling reports. The samples provide important constraints for correlation to surrounding stratigraphy, static reservoir models, calculation of hydrocarbons in place and geo-steering decisions. This process is time-consuming which limits the time from cuttings collection to actionable information. In addition, materials characterization may vary from one well-site geologist to the next.

SUMMARY

Accordingly, a need exists for methods of analyzing geologic samples in realtime to determine mineralogy, organic content, hydrocarbon presence, or combinations thereof of a geologic sample. The present disclosure addresses this need by incorporating both onsite analysis equipment and midwave infrared wavelengths or ultraviolet wavelengths for determining mineralogy, organic content, hydrocarbon presence, or combinations thereof of a geologic sample. Cuttings analysis, lithology identification, and hydrocarbon detection using multi-range hyperspectral scanning allows wellsite geologists to acquire quantitative data quickly and efficiently, reducing the time needed for characterization and analysis at the wellsite. This disclosure describes methods for rapid and automated lithology determination and hydrocarbon detection from samples in real time using multi-range hyperspectral scanning. The data acquired are both numeric (spectral) and visual (samples imagery, that shows, for example, the texture of the rock fabric at the resolution of the scanner), therefore making it ideal for quantitative assessment using computational workflows for cuttings analysis.

In accordance with one embodiment of the present disclosure, a method of analyzing a geologic sample includes illuminating the geologic sample with a light beam. The light beam may include a light source or series of light sources that cover the full spectral range of interest (i.e. lamps, tunable lasers, LEDs, and the like. The method further includes capturing an image of the geologic sample on a hyperspectral camera or series of hyperspectral cameras thereby collecting spectra reflected form a surface of the geologic sample, the spectra having mid-wave infrared wavelengths, visible light wavelengths, ultraviolet wavelengths, or combinations thereof. In addition a fluorescence imaging capability that includes a UV excitation source and detect the fluorescence emission from the geology sample. The method further includes processing the image to transform the image from R-G-B color space to Intensity, thereby transforming the spectra into a distribution of relative intensities of fluorescence or absorbance at the varied wavelengths and analyzing the Intensity or absorbance to determine mineralogy, organic content, hydrocarbon presence, or combinations thereof of the geologic sample.

In another embodiment of the present disclosure, a method of analyzing a geologic sample includes drilling a wellbore, acquiring the geologic sample from the wellbore, and placing the geologic sample in a plate reader. The method further includes illuminating the geologic sample with a light beam and capturing an image of the geologic sample on a hyperspectral camera thereby collecting spectra reflected from a surface of the geologic sample, the spectra having varied wavelengths comprising mid-wave infrared wavelengths, visible light wavelengths, ultraviolet wavelengths, or combinations thereof. The method further includes processing the image to transform the image from R-G-B color space to Intensity, thereby transforming the spectra into a distribution of relative intensities of fluorescence or absorbance at the varied wavelengths, and analyzing the Intensity to determine mineralogy, organic content, hydrocarbon presence, or combinations thereof of the geologic sample.

BRIEF DESCRIPTION OF THE DRAWINGS

The following detailed description of specific embodiments of the present disclosure can be best understood when read in conjunction with the following drawings, in which.

DETAILED DESCRIPTION

Figure 1:
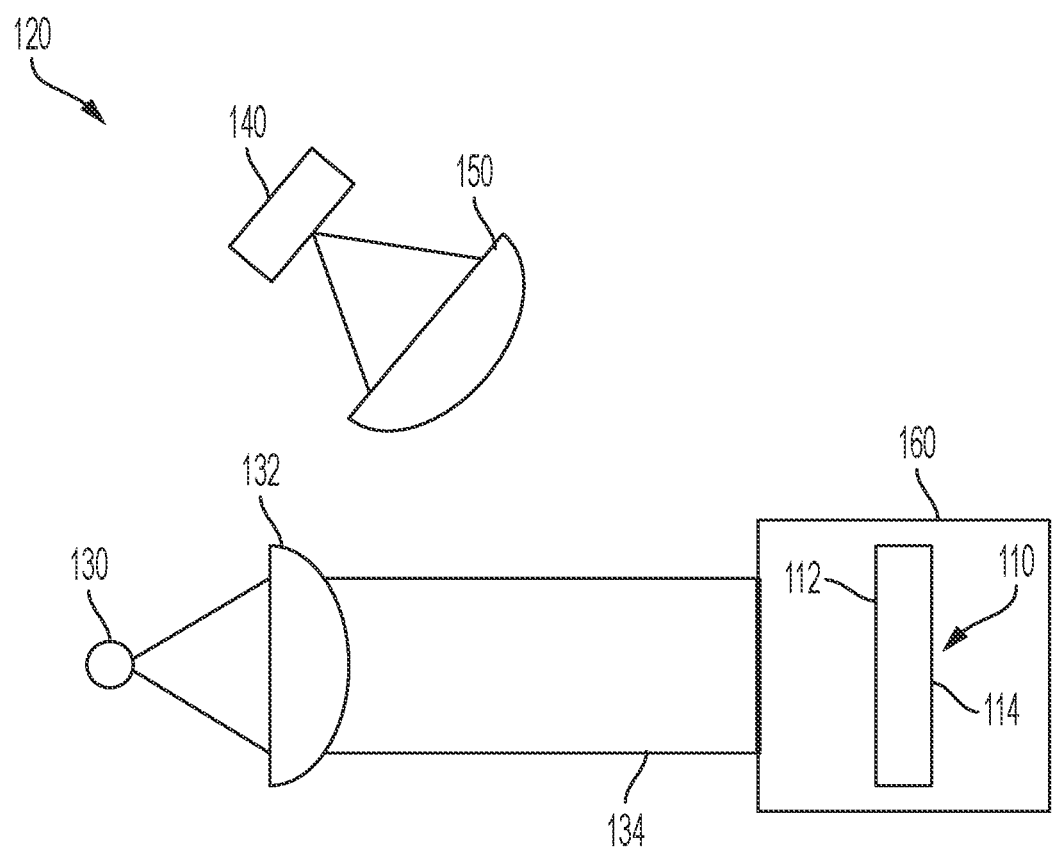
FIG. 1 schematically illustrates a system for capturing images according to one or more embodiments described herein.

Embodiments of the present disclosure are directed to methods of analyzing a geologic sample.

A formation is the fundamental unit of lithostratigraphy. As used in the present disclosure, the term "formation" refers to a body of rock that is sufficiently distinctive and continuous from the surrounding rock bodies that the body of rock can be mapped as a distinct entity. A formation is, therefore, sufficiently homogenous to form a single identifiable unit containing similar lithological properties throughout the formation, including, but not limited to, porosity and permeability. A single formation may include different regions, where some regions include hydrocarbons and others do not. To produce hydrocarbons from the hydrocarbon regions of the formation, production wells are drilled to a depth that enables these hydrocarbons to travel from the subsurface formation to the surface and or lateral extensions are added to increase reservoir contact. When needed fracturing can also be used to improve contact. In some cases core is collected while drilling the vertical sections. In most cases, cuttings can be collected while drilling both the vertical and lateral portions of the well.

As stated previously, embodiments of the present disclosure are directed to methods of analyzing a geologic sample. The method may include drilling a wellbore. The method may include preparing a drilling fluid by combining a liquid carrier with a clay-based material. As used throughout this disclosure, the term "clay-based material" can refer to barite, bentonite, barite, or barium sulfate, as nonlimiting examples. These clay-based materials will increase the density or viscosity of the drilling fluid. The drilling fluid may be introduced into the subsurface formation through a drilling assembly. The drilling assembly may include a drilling platform that supports a derrick having a traveling block for raising and lowering a drill string. The drill string may include, but is not limited to, drill pipe and coiled tubing, as generally known to those skilled in the art. As used throughout this disclosure, the term "drill string" refers to the combination of the drill pipe, the bottomhole assembly and any other tools used to drill the wellbore or introduce fluid into the wellbore. As used throughout this disclosure, the term "coiled tubing" refers to a long, continuous length of pipe wound on a spool. The pipe is straightened prior to pushing into a wellbore and rewound to coil the pipe back onto the transport and storage spool. Depending on the pipe base diameter (1 in. to 4½ in.) and the spool size, coiled tubing can range from 2,000 ft to 15,000 ft (610 to 4,570 m) or greater length. A kelly may support the drill string as it is lowered through a rotary table. As used throughout this disclosure, the term "kelly" refers to a long square or hexagonal steel bar with a hole drilled through the middle for a fluid path. The kelly is used to transmit rotary motion from a rotary table or kelly bushing to the drillstring, while allowing the drillstring to be lowered or raised during rotation. A drill bit is attached to the distal end of the drill string and is driven either by a downhole motor or via rotation of the drill string from the well surface, or by both. As the bit rotates, it creates a wellbore that penetrates various subsurface formations.

A pump (e.g., a mud pump) circulates drilling fluid through a feed pipe and to the kelly, which conveys the drilling fluid downhole through the interior of the drill string and through one or more orifices in the drill bit. The drilling fluid is then circulated back to the surface via an annulus defined between the drill string and the walls of the wellbore. As used throughout this disclosure, the term "drill pipe" refers to a tubular steel conduit fitted with special threaded ends called tool joints. The drill pipe connects the rig surface equipment with the bottomhole assembly and the bit, both to pump drilling fluid to the bit and to be able to raise, lower and rotate the bottomhole assembly and bit. At the surface, the recirculated or spent drilling fluid exits the annulus and may be conveyed to one or more fluid processing units via an interconnecting flow line. After passing through the fluid processing units, a "cleaned" drilling fluid is deposited into a nearby mud pit. While illustrated as being arranged at the outlet of the wellbore via the annulus, those skilled in the art will readily appreciate that the fluid processing units may be arranged at any other location in the drilling assembly to facilitate its proper function, without departing from the scope of the disclosure.

The method may include acquiring the geologic sample from the wellbore. Acquiring the geological sample from the wellbore may include coring, collecting cuttings, or both. In embodiments, the method may further include cleaning the geologic sample. Cleaning the geologic sample may include flushing the geologic sample with a solvent. The solvent may be chosen from the group consisting of acetone, chloroform, methanol, cyclohexane, ethylene chloride, methylene chloride, naphtha, tetrachloroethylene, tetrahydrofuran, toluene, trichloroethylene, xylene, or combinations thereof.

Referring now to FIG. 1, the geologic sample 100 may be illuminated with a light beam 134. In embodiments, the light beam 134 may be formed by an imaging apparatus. The imaging apparatus 120 may include a light source 130, an image sensor 140, and a focusing lens 150. As used herein, "upstream" and "downstream" refer to the relative position of two locations or components along a light pathway with respect to a light source. For example, a first component is upstream from a second component if the first component is closer to the light source along the path traversed by the light beam than the second component.

As stated previously, the imaging apparatus 120 may include a light source 130. In embodiments, the light source 130 may include non-collimated light source or a collimated light source, meaning that the rays of the collimated light are substantially parallel. The light source 130 may include lasers (single wavelength) or multi-wavelength lamp light sources. In embodiments, the light source 130 may have a spot size of from 1 to 10 nm, from 1 to 5 nm, from 1 to 3 nm, from 2 to 10 nm, from 2 to 5 nm, from 2 to 4 nm, from 2 to 3 nm, from 3 to 5 nm, from 3 to 4 nm, or of about 3 nm.

In embodiments, a collimating lens 132 may be integrated with the light source 130, forming a collimated light beam. In embodiments, a collimating lens 132 may be positioned downstream of the light source 130 to collimate the light beam emitted from the light source 130. A collimating lens 132 is an optical lens that aligns a beam of light (or reduced divergence in the beam path) to cause the directions of motion of light particles to become more aligned in a specific direction. In other words, a collimating lens 132 forms parallel rays of light, thereby forming a beam of collimated light.

As stated previously, the imaging apparatus 120 may include an image sensor 140 and a focusing lens 150. In some embodiments, the focusing lens 150 may be a telecentric lens. Conventional lenses have angular fields of view, which means that as the distance between the lens and object increase, the magnification decreases. This angular field of view results in parallax error, also known as perspective error. Telecentric lenses eliminate this parallax error by having a constant, non-angular field of view. With telecentric lenses, magnification remains constant with object displacement, provided the object stays within the telecentric range, meaning the total distance above and below an object that remains in focus and at constant magnification.

The focusing lens 150 may be optically coupled to the image sensor 140. The image sensor 140 includes a hyperspectral camera. The image sensor 140 may have a pixel count of at least 10 megapixels, allowing the image sensor 140 to capture high resolution images. In embodiments, the pixel count may be as low as 16 by 16 pixels, 256 by 256 pixels, 640 by 480 pixels, 1024 by 768 pixels, 1280 by 1024 pixels, 1920 by 1080 pixels, or 4064 by 2704 pixels.

In embodiments, the light source 130 and the image sensor 140 may be positioned on opposite sides of the geologic sample 110, and particularly on opposite sides of the geologic sample 110, such that the light source 130 may pass through the sample chamber 160 and the geologic sample 110 to be captured by the focusing lens 150 and the image sensor 140. In embodiments, the imaging apparatus 120 configuration surrounding the geologic sample 110 may be reversed.

In embodiments, the imaging apparatus 120 may acquire images of the geologic sample. The images acquired by the imaging apparatus 120 may be processed to determine the mineralogy, organic content, hydrocarbon presence, or combinations thereof of the geologic sample.

As previously stated, the method includes illuminating the geologic sample with the light beam 134. The method further includes capturing an image of the geologic sample 110 on an image sensor 140, thereby collecting spectra reflected from a surface of the geologic sample. The spectra may have varied wavelengths, the varied wavelengths including mid-wave infrared wavelengths, visible light wavelengths, ultraviolet wavelengths, or combinations thereof reflected from the surface of the geologic sample.

The mid-wave infrared wavelengths may range from 2000 to 6000 nanometers (nm), from 2000 to 5500 nm, from 2000 to 5000 nm, from 2000 to 4500 nm, from 2000 to 4000 nm, from 2000 to 3500 nm, from 2000 to 3000 nm, from 2000 to 2500 nm, from 2500 to 6000 nm, from 2500 to 5500 nm, from 2500 to 5000 nm, from 2500 to 4500 nm, from 2500 to 4000 nm, from 2500 to 3500 nm, from 2500 to 3000 nm, from 3000 to 6000 nm, from 3000 to 5500 nm, from 3000 to 5000 nm, from 3000 to 4500 nm, from 3000 to 4000 nm, from 3000 to 3500 nm, from 3500 to 6000 nm, from 3500 to 5500 nm, from 3500 to 5000 nm, from 3500 to 4500 nm, from 3500 to 4000 nm, from 4000 to 6000 nm, from 4000 to 5500 nm, from 4000 to 5000 nm, from 4000 to 4500 nm, from 4500 to 6000 nm, from 4500 to 5500 nm, from 4500 to 5000 nm, from 5000 to 6000 nm, from 5000 to 5500 nm, or from 5500 to 6000 nm. When the mid-wave infrared wavelengths contact the geologic sample 110, the absorbance of the light at each wavelength is detected as related to the vibrational spectroscopy of the functional groups present.

The ultraviolet wavelengths may range from 100 to 400 nm, from 100 to 350 nm, from 100 to 300 nm, from 100 to 250 nm, from 100 to 200 nm, from 100 to 150 nm, from 150 to 400 nm, from 150 to 350 nm, from 150 to 300 nm, from 150 to 250 nm, from 150 to 200 nm, from 200 to 400 nm, from 200 to 350 nm, from 200 to 300 nm, from 200 to 250 nm, from 250 to 400 nm, from 250 to 350 nm, from 250 to 300 nm, from 300 to 400 nm, from 300 to 350 nm, or from 350 to 400 nm. When the ultraviolet wavelengths contact the geologic sample 110, the intensity of the fluorescence is then imaged.

The visible light wavelengths may range from 400 to 1000 nm, from 400 to 900 nm, from 400 to 700 nm, from 400 to 500 nm, from 500 to 1000 nm, from 500 to 900 nm, from 500 to 700 nm, from 700 to 1000 nm, from 700 to 900 nm, or from 900 to 1000 nm. When the visible light wavelengths contact the geologic sample 100, the intensity of the fluorescence is then imaged.

In embodiments, the image may be captured by a hyperspectral camera comprising the image sensor 140 and the focusing lens 150, where the geologic sample 110 is positioned within a field of view of the hyperspectral camera. The "field of view" as used herein refers to size of the area on a plane perpendicular to the optical path in the object space at a distance along the optical path that is in focus being imaged on the image sensor 140. In embodiments, the image may be captured by a series of hyperspectral cameras. Hyperspectral cameras collect a spectrum or spectra at many locations on the sample. When more than one wavelength range is used, a series of hyperspectral cameras may be used that are designed for the specific wavelengths ranges used and each paired with the applicable light source. A non-limiting example of a hyperspectral camera is the ViaSpec™ Geo Series Hyperspectral Multi-range Scanner Systems available from Middleton Spectral Vision.

Hyperspectral imaging collects and processes information from across the electromagnetic spectrum. The goal of hyperspectral imaging is to obtain the spectrum for each pixel in the image of a scene, with the purpose of finding objects, identifying materials, or detecting processes. There are three general branches of spectral imagers. There are push broom scanners and whisk broom scanners (spatial scanning), which read images over time, band sequential scanners (spectral scanning), which acquire images of an area at different wavelengths, and snapshot hyperspectral imaging, which uses a staring array to generate an image.

Minerals develop spectral signatures in the various spectral regions. For the various spectral regions there are optical instruments that can record the visible, infrared and other characteristic spectra of minerals. Based on the spectral information, the different materials can be identified from previously recorded spectral libraries. These spectral libraries may include previously recorded sets of other spectral information, such as Absorbance and Intensity distributions, correlated with specific mineralogies by visual or chemical analysis. Hyperspectral imaging of geologic samples have been measured with different spectroscopic methods but the conventional methods only measure an average of an area or a small section of the available surface of the sample. Hyperspectral imaging is capable of exploring the spectral signatures of each point of samples. The spatial distribution of the specific minerals obtained using hyperspectral imaging describes not only the composition and location of the minerals but the genesis of the geologic samples can be inferred from the images. One sample presentation for hyperspectral imaging is the sectioning of the approximately 4 inch diameter core samples. The core samples are placed in a holder that positions the flat cut surface perpendicular to the observing hyperspectral cameras. All of the hyperspectral imaging cameras applied by the Via Spec-Geo are push-broom type. Using this technique, the sample needs to be moved under the observation line of the cameras at a uniform slow rate. A hypercube of data is collected line-by-line from the whole measured surface. The data contains the respective spectra for each point of the sample.

Hyperspectral imaging combines digital imagery for spatial information and reflectance spectroscopy for chemical information. The versatility of the imaging system allows for geologic samples of any shape or size to be characterized. The geologic sample may include cuttings, core plugs, whole core (unslabbed or slabbed), or combinations thereof. Digital images may be acquired in conjunction with reflectance spectroscopy measurements that correspond to each pixel of the image.

In embodiments, the hyperspectral camera may include a pushbroom imaging spectral sensor. A pushbroom scanner, also known as an along-track scanner, is a device for obtaining images with spectroscopic sensors. In embodiments, a line of sensors arranged perpendicular to a direction of movement may be used, where different areas of the surface are imaged as the object continues in a direction of motion. A pushbroom scanner may gather more light than a whisk broom scanner because a pushbroom scanner scans a particular area for a relatively longer time, than a whisk broom scanner.

In embodiments, capturing the image may further include pushbroom detection and spatial line scanning. In spatial line scanning, each two-dimensional (2-D) sensor output represents a full slit spectrum (x,λ). The hyperspectral camera may obtain slit spectra by projecting a strip of the scene onto a slit and dispersing the slit image with a prism or a grating. Each detector collects a line of data then the belt moves the sample and another line of data is collected. When working with many spectral ranges the belt timing and distance is known so that the data from one line on one detector can later be aligned with the data from one line on the other detectors. In general this alignment can be done by any known mechanical movement and timing but can also be done through signal processing to align and orient image/data features in the data processing domain. The image may then be analyzed per lines with the pushbroom scanner. Specifically, each detector collects a line of data then the belt moves the sample and another line of data is collected. When working with many spectral ranges the belt timing and distance is known so that the data from one line on one detector can later be aligned with the data from one line on the other detectors. In general this alignment can be done by known mechanical movement and timing but can also be done through signal processing to align and orient image/data features in the data processing domain.

The hyperspectral camera may image the sample onto a slit of a transmission spectrograph. The spectrograph produces a spectrum imaged on a focal plane array detector, preserving the location of respective points on the slit and thus the points of the line on the sample. Successive lines on the sample measured over time form a complete hyperspectral dataset. This data from a hyperspectral camera is called a "hypercube" containing information in two spatial dimensions and one spectral dimension. The hypercube is typically processed with similar hypercube measurements of a highly reflective white reference material and the residual background signal, the latter of which is measured when no light is falling on the focal plane array. The resultant corrected spectra are produced in transmittance, reflectance or absorbance similar to traditional spectroscopic measurements. The results can be further processed, scaled, smoothed, and eventually compressed to produce the information that can be used for measurements, such as composition, color coordinates or thickness.

In embodiments, the method may include placing the geologic sample in a plate reader. The sample chamber 160 may include a plate reader. In embodiments, the plate reader may include a multi-well plate reader. In a multi-well plate reader samples are placed in 6, 12, 48, or 96 wells within the plate. The wells may fit 1 inch plugs, which may provide some of the textural information from the subsurface formation, which may not be provided by cuttings. Each plate has the same total spatial footprint (conventionally 128 millimeters (mm) by 85 mm), such that as the number of wells within the plate increases, the well size decreases.

The plate reader may include a filter-based multimode microplate that includes several sets of optical filters. When a filter-based multimode microplate is used, light from the light source is passed through a filter on the excitation side, which typically transmits at least 60% of the desired wavelength in the visible range to the sample well. The light excites the sample, which in return emits a specific fluorescent signal according to its unique properties. An emission filter, coupled with a dichroic mirror in some cases, cleans the sample's signal and typically transmits at least 60% of the desired wavelength to the detector. A filter-based reader is more effective at delivering light to the sample and light blocking between the excitation and emission channels for superior sensitivity. Bandwidth selection is an advantage as a filter can be dedicated to a specific assay for maximum sensitivity and can have a bandwidth from a few nanometers to greater than 100 nm, which is necessary for low-level fluorescence assays. Additionally, filter-based microplate readers can rapidly switch between two wavelengths, or be designed with two measurement channels, for ratiometric-based assays while monochromator-based systems are typically much slower.

The plate reader may include a monochromator-based microplate reader, which uses diffraction gratings instead of filters to deliver a wavelength to the sample. White light is reflected by one or more diffraction gratings on the excitation side. Each grating has an average efficiency of about 40% at the desired wavelength, so the total efficiency of the two gratings is about 16%. The light excites the sample in the well, which in turn emits a specific fluorescent signal. An emission monochromator cleans the signal through another diffraction grating or set of diffraction gratings, with a combined efficiency of approximately 16%, before sending the signal to a detector. The combined excitation/emission efficiency of this system is much lower compared to the efficiency of a filter-based design.

In embodiments where a plate reader is used, the optics in the plate reader may be focused and rastered through each well in the plate. The reflected light is collected by detectors such as photomultiplier tubes, CCD, EMCCD, or CMOS. The light can be set to illuminate each well individually or to more broadly illuminate the sample. This could be done with a fiber optic cable or various mirrors and lenses to focus the light if whole tray illumination is not desired. For the vibrational spectroscopy that happens in the MWIR or hyperspectral ranges the difference in the intensity at each wavelength reflected versus that of the source light is used to determine the absorbance at each wavelength to produce a spectrum. In the case of fluorescence a narrower band of UV light or a laser would be used to excite the fluorescence response from the sample. The fluorescent light emitted (from visible to near infrared wavelengths) from the sample may be detected by a detector as described above. A separate data set is collected at either a single point or multiple points in each well, which can be averaged or compared to understand sample variation. The spectra from all wells can be averaged if all wells contain the same sample or used as a high-throughput screening tool when the sample in each well differs.

In embodiments, the same mass or volume of geologic sample may be added to each well of the plate reader. The geologic sample may be added to the wells manually or with a robotic sampler. In some configurations, the optics can be adjusted to focus on the sample in each well separately if the height of the sample varies from one well to the next. In embodiments, each well in a single plate may be filled with the same depth of samples, such that the data from all wells in the plate may be averaged for better statistics. At the other extreme each well could be filled with a sample from a different depth interval which would provide fewer statistics but would allow a fast acquisition over a range of depths. Other variations exist where the plate could be filled by row, column, or preselected number of wells per depth. The well plate would then run through a series of separated plate readers or a system that is configured similarly to the large lab-scale device described above, covering the spectral characterization ranges of interest or other spectroscopic methods such as Raman spectroscopy to identify hydrocarbon shows, lithology, thermal maturity, and hydrocarbon quality (such as API gravity), or combinations thereof.

In embodiments, the image may include an image of a surface of the geologic sample 110. For example, the image may include an image of the front surface 112 of the geologic sample 110. The method may further include capturing one or more additional images of the geologic sample from one or more additional surfaces. For example, the method may further include capturing an image of the back surface 114 of the geologic sample 110. In embodiments, the method may further include transporting the geologic sample 110 to an additional imaging apparatus where the additional imaging apparatus captures an additional image of the geologic sample 110 from an additional surface. For example, an image of the front surface 112 of the geologic sample 110 may be captured by a first imaging apparatus, and then the geologic sample 110 may be transported to a second imaging apparatus, where an image of the back surface 114 of the geologic sample 110 is captured. In embodiments, transporting the geologic sample 110 may include an automated conveyor belt positioned to transport the geologic sample 110 between multiple imaging apparatuses. It is contemplated that images may be captured of all sides of the geologic sample, such as the front surface 112, the back surface 112, a side surface, a top surface, or a bottom surface. In embodiments, there may be from 1 to 6, from 1 to 5, from 1 to 4, from 1 to 3, from 2 to 6, from 2 to 5, from 2 to 4, from 3 to 6, from 3 to 5, or from 4 to 6 imaging apparatuses to capture images of the geologic sample. In embodiments, there may be 1, 2, 3, 4, 5, or 6 imaging apparatuses to capture images of the geologic sample.

In embodiments, the image of the geologic sample 110 captured on the image sensor 140 may be captured as a greyscale image made up of individual pixels. Each individual pixel may include an observed voltage associated with the entire spectra recorded by the hyperspectral camera. The spectra may include visible and near-infrared wavelength spectra (VNIR), short wave infrared wavelength spectra (SWIR), mid-wave infrared spectra (MWIR), or combinations thereof. In this way, the spectra may include wavelength spectra from 100 nm to 6000 nm. The voltage may then be transformed into an Intensity. In embodiments, the image of the geologic sample 110 captured on the image sensor 140 may also be captured in an R-G-B color space image. In embodiments, the R-G-B color space may be assigned to the data collected by the detectors described above, to estimate compositional variations based on the data available (such as the intensity of the peaks or area under the peaks) in each of the spectral ranges. In embodiments, the method may further include processing the image, whether greyscale or R-G-B color space, captured on the image sensor 140 to transform the image to Intensity.

Figure 2:
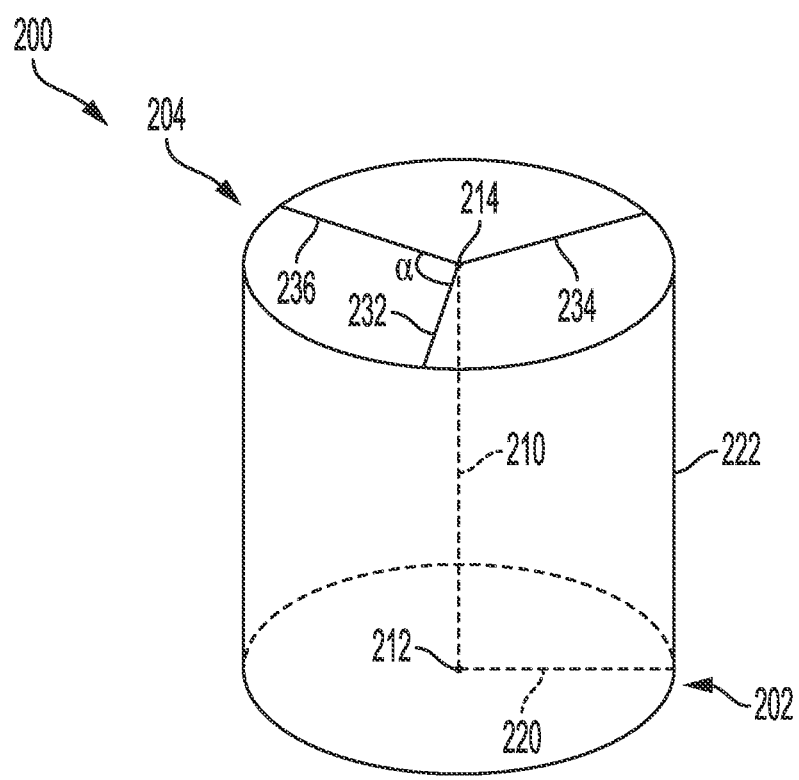
FIG. 2 schematically illustrates a Hue model according to one or more embodiments described herein.

In embodiments, transforming the image to Intensity may include processing the image to transform the image from R-G-B color space to Hue Saturation and Intensity (HSI). As used herein, "Hue," when used alone, refers to any of HSI. Without intending to be bound by theory, in Hue models, colors of each hue are arranged in a radial slice, around a central axis of neutral colors. In embodiments, Hue models may be represented by cylindrical geometries, such as the cylinder 200 shown in FIG. 2. A central axis 210 of the cylinder comprises neutral colors ranging from black at one end of the central axis 210 (generally the bottom end 212 of the central axis 210 at the bottom 202 of the cylinder 200) to white at the other end of the central axis 210 (generally the top end 214 of the central axis 210 at the top 204 of the cylinder 200). This central axis 210 may represent intensity, lightness, value, or brightness, ranging from 0 to 1. The Hue model may further include a saturation dimension 220 radiating outwards from the central axis 210, where saturation is 0 at the central axis 210 and saturation is 1 at the circumference 222 of the Hue cylinder. The hues within the Hue models may be represented in angular dimensions a surrounding the central axis 210, where the red primary 232 is positioned at 0°, the green primary 234 is positioned at 120°, and the blue primary 236 is positioned at 240°. In embodiments, the angular dimensions a may be expressed in a value from 0 to 1 as a fraction of the range of 0 to 360.

Processing the image to transform the image to Intensity may include any process known in the art. In embodiments, this may include using software such as Matlab. Transforming the greyscale image or the R-G-B color space to Intensity may also transform the spectra that was recorded by the hyperspectral camera into a distribution of relative intensities of fluorescence at the varied wavelengths recording by the hyperspectral camera. In embodiments, the method may further include analyzing Intensity to determine mineralogy, organic content, hydrocarbon presence, or combinations thereof of the geologic sample. In embodiments, Intensity values may be represented from 0 to 1 as the relative intensity of varying wavelengths of light. The Intensity values may take the form of various peaks and valleys of the relative intensities, as illustrated for example by FIGS. 4 and 7-10. Analyzing the Intensity may then further involve analyzing the relative intensity under the various peaks, as well as the area underneath the various peaks.

Variations in mineralogy produce changes in the absorbance versus wavelength curve shape and may include the appearance or loss of specific peaks or mild shifts in peak position, which may be used for detecting organic components and hydrocarbons. For wavelengths ranging from 2000 to 6000 nm, changes in the peak positions or relative intensity or magnitude of certain peaks can be used to provide a quantitative or qualitative assessment of the thermal maturity of residual organic matter (i.e. kerogen, bitumen, etc) in source rocks (unconventional reservoir rocks) or the presence of hydrocarbons in conventional reservoir rocks (i.e. sandstones and carbonates) where residual organic matter is not present. Finally, fluorescence in wavelengths from 400 to 800 nm is known to vary with organic matter thermal maturity as well as hydrocarbon content and quality. It is contemplated that, in samples that include solid organic matter the fluorescence varies with thermal maturity and organic matter content, and in samples saturated with hydrocarbons, the fluorescence varies with hydrocarbon content and API gravity. Therefore, mineralogy, organic content, and hydrocarbon presence may be determined by comparing the Intensity of the image of the geologic sample to the spectral library, specifically previously recorded Intensities within the spectral library.

For example, and in embodiments, analyzing the Intensity to determine mineralogy may include comparing the Intensity to the spectral library, the spectral library comprising previously recorded Intensities associated with specific mineralogy. It may further include choosing a best match of the previously recorded Intensities to the Intensity of the image of the geologic sample. Finally, it may further include determining the mineralogy of the geologic sample based on the mineralogy of the best match. For example, if the best match to the Intensity is a sample with mudstone mineralogy, then the mineralogy of the geologic sample may be regarded as a mudstone.

Further, analyzing the Intensity to determine organic content may include comparing the relative intensity in the wavelength range of 2000 to 6000 nm of the Intensity to the best match of the previously recorded Intensities; observing differences in the relative intensity of the geologic sample versus the best match of the previously recorded Intensities, the differences comprising changes in peak positions or magnitude of peaks within the Intensity; and determining the organic content of the sample based on the differences, wherein the organic content is a qualitative assessment of the thermal maturity of the organic matter making up the organic content. For example, if the relative intensity of the geologic sample is greater than that for the best match previously recorded Intensity over the same wavelength range, the geologic sample may be regarded as containing at least some organic content. Further, and as previously discussed, as the degree of separation between the geologic sample and the best match increases, the organic content of the geologic sample may be determined to be more thermally mature.

It is further contemplated that by calibrating the geologic sample with the best match and another geologic sample of known organic content with similar mineralogy from the spectral library, a quantitative assessment of the total percentage organic content may be determined. Calibration methods may include but are not limited to: partial-least-squares regression (PLSR), support vector regression (SVR), and multivariate adaptive regression splines (MARS). The calibration methods may also include pre-processing techniques, such as one or more of: Savitzky-Golay (SG) smoothing, first derivative with SG smoothing (FD-SG), second derivative with SG smoothing (SD-SG), continuum removed reflectance (CR), standard normal variate and detrending (SNV-DT), multiplicative scatter correction (MSC), and extended MSC.

Further yet, analyzing the Intensity to determine hydrocarbon presence may include comparing the relative intensity in the wavelength range of 400 to 800 nm of the Intensity to the best match of the previously recorded Intensities; observing differences in the relative intensity of the geologic sample versus the best match of the previously recorded Intensities, the differences comprising changes in peak positions or magnitude of peaks within the Intensity; and determining the hydrocarbon presence of the sample based on the differences, wherein the hydrocarbon presence is a quantitative assessment of the presence and amount of hydrogen-carbon bonds present within the geologic sample. For example, similar to that for organic content, if the relative intensity of the geologic sample is greater than that for the best match previously recorded Intensity over the same wavelength range, the geologic sample may be regarded as having the presence of hydrocarbons within.

Further, as the degree of separation between the geologic sample and the best match increases, more hydrocarbons may be regarded as being present within the geologic sample.

Similar to that for the organic content, a quantitative assessment of the total percentage hydrocarbon content in the geologic sample may be conducted by calibrating the geologic sample with the best match and another geologic sample of known hydrocarbon content with similar mineralogy from the spectral library. Calibration methods may include any of those previously stated.

When combined, the information from hyperspectral image maps can provide a fast, non-destructive method to analyze cuttings as well as other materials such as core, core plugs, soils, and well-site fluids.

EXAMPLES

The analysis of geologic samples according to the systems and methods described herein were conducted.

A feasibility study was conducted to provide examples of the utility of the multi-range hyperspectral scanning system for cuttings assessment. Several different rock types were scanned and spectral maps were generated to demonstrate the utility of the method to determine rock mineralogy. In addition, source rock samples were artificially matured to document the changes in spectral response associated with hydrocarbon generation. As shown herein, the spectral techniques presented may be regarded as a significant improvement over destructive laboratory analysis, as they are capable of providing quantitative information about lithology, rock type, relative organic thermal maturity and hydrocarbon presence.

Figure 8:
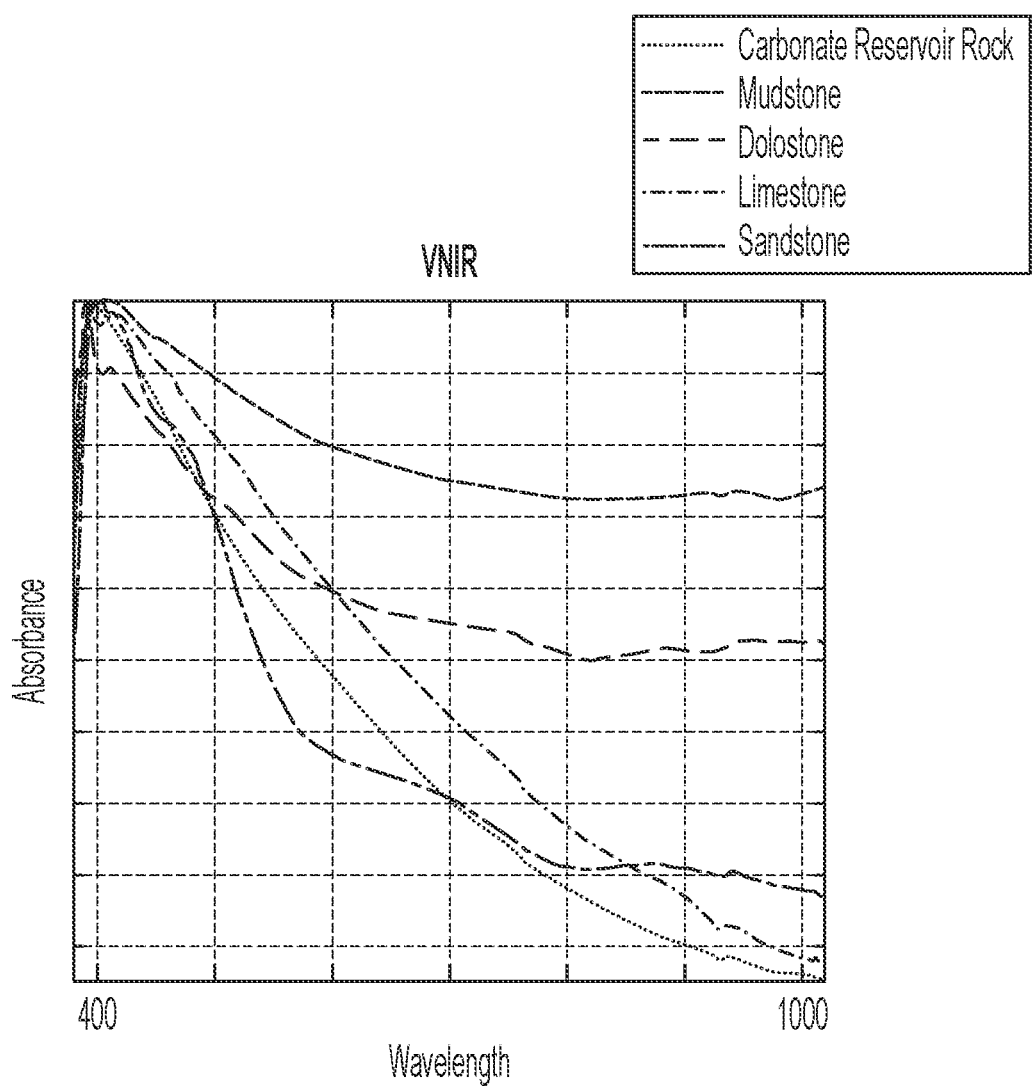
FIG. 8 graphically illustrates the mean absorbance distribution of rock samples according to one or more embodiments described herein.
Figure 9:
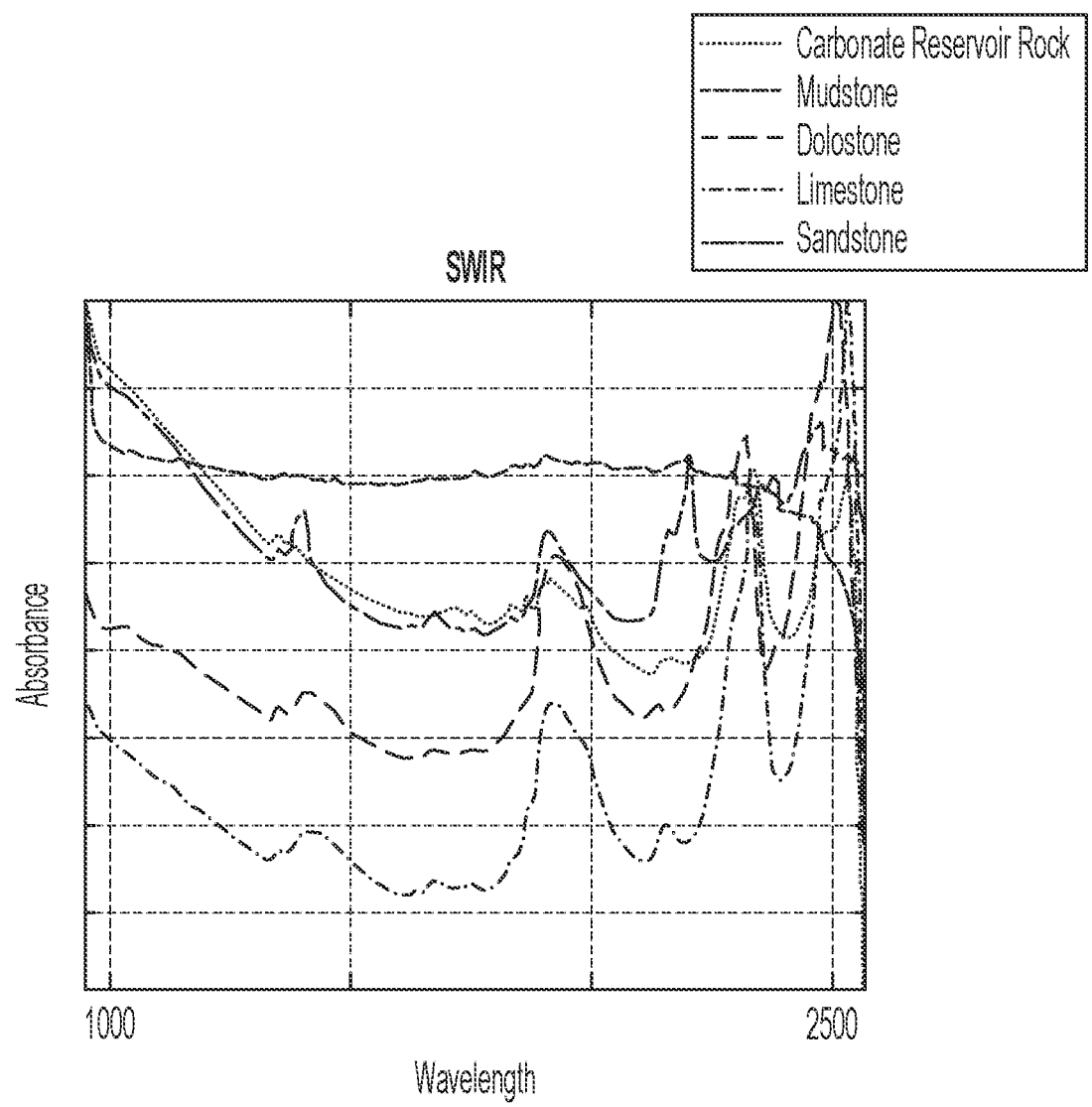
FIG. 9 graphically illustrates the mean absorbance distribution of rock samples according to one or more embodiments described herein.
Figure 10:
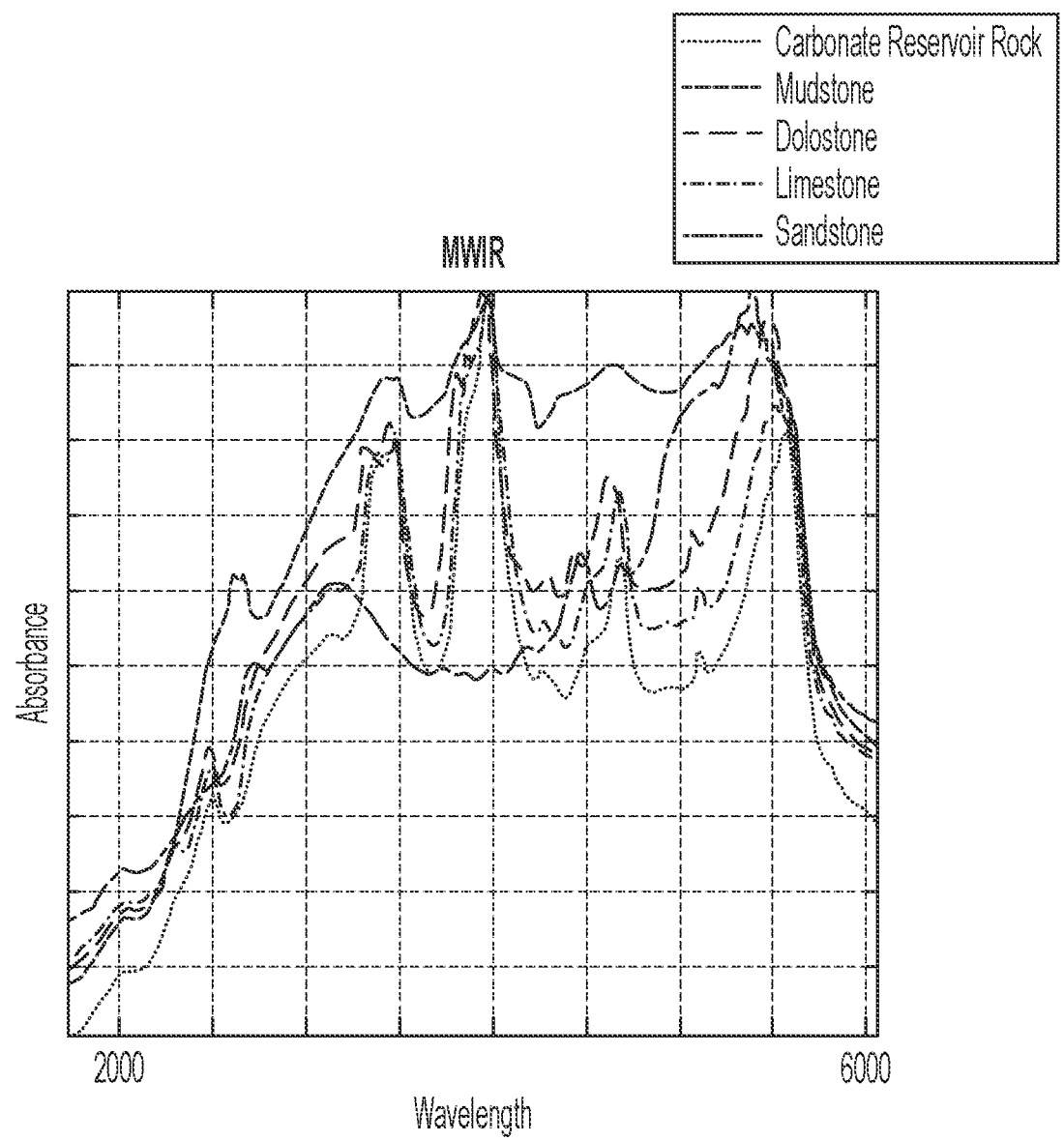
FIG. 10 graphically illustrates the mean absorbance distribution of rock samples according to one or more embodiments described herein.
Figure 11:
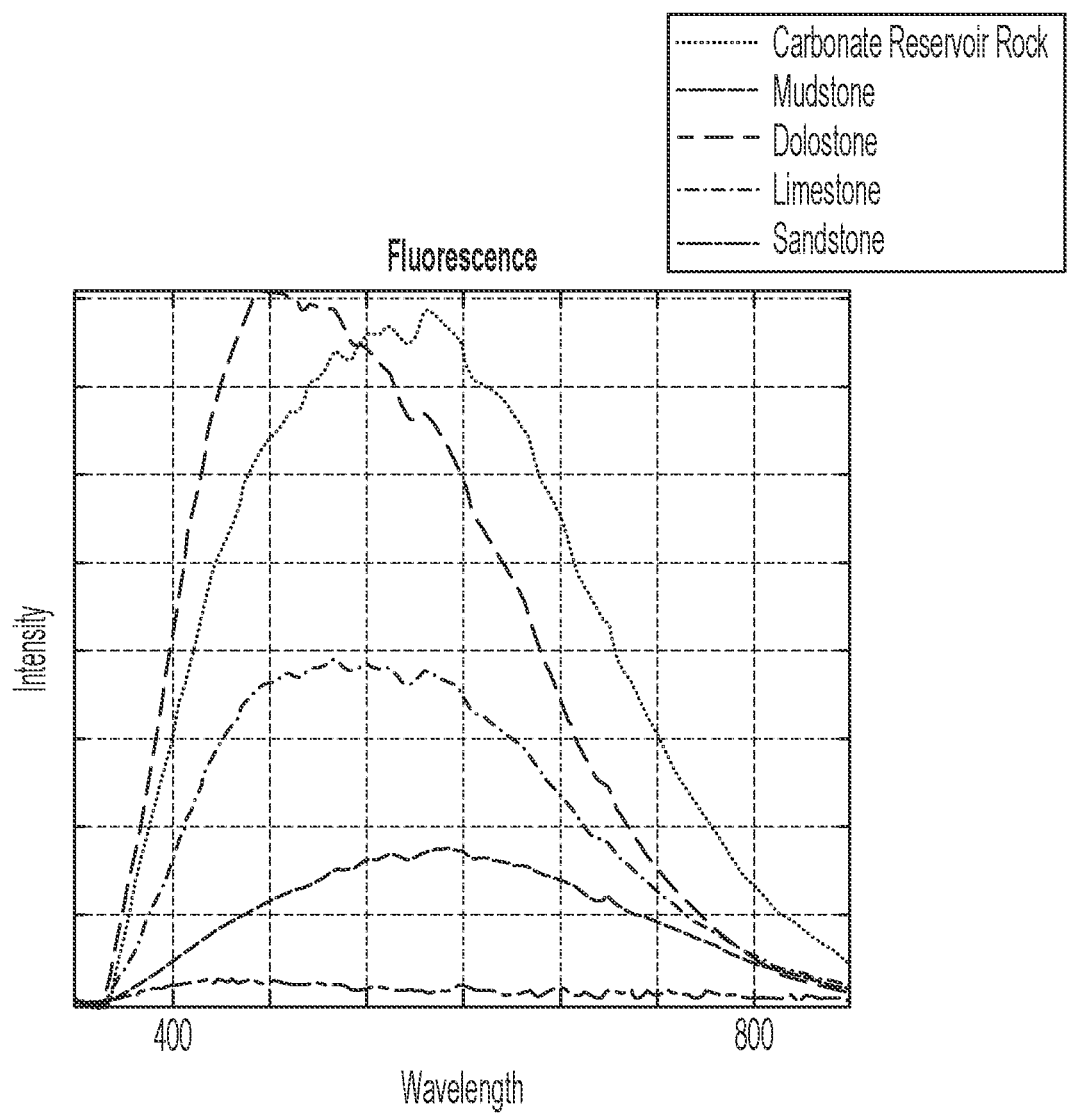
FIG. 11 graphically illustrates the mean intensity distribution of rock samples according to one or more embodiments described herein.

Representative spectral maps were formed for several reservoir rock types including A) carbonate reservoir rock, B) mudstone, C) dolostone, D) limestone and E) a clean sandstone. The intensity maps represent the mean percent reflectance (average intensity of the spectrum across all pixels) or mean percent absorbance (average absorbance of the spectrum across all pixels). FIG. 8 illustrates the relative absorbance across the visible and near-infrared wavelength spectra (VNIR). FIG. 9 illustrates the relative absorbance across the short wave infrared wavelength spectra (SWIR). FIG. 10 illustrates the relative absorbance across the Mid-wave Infrared spectra (MWIR). FIG. 11 illustrates the relative intensity (fluorescence) across the visible and near-infrared wavelength spectra. The spectras clearly show not only differences in absorbance but also characteristic absorption features (peaks) related to the different rock types. The carbonate reservoir rock was composed of primarily (>50%) carbonates (limestone), but with minority (<50%) sandstone, mudstone, and dolostone contents. Accordingly, the carbonate reservoir rock may be observed to have a different spectra signature than any of the other singular rock types.

Figure 3:
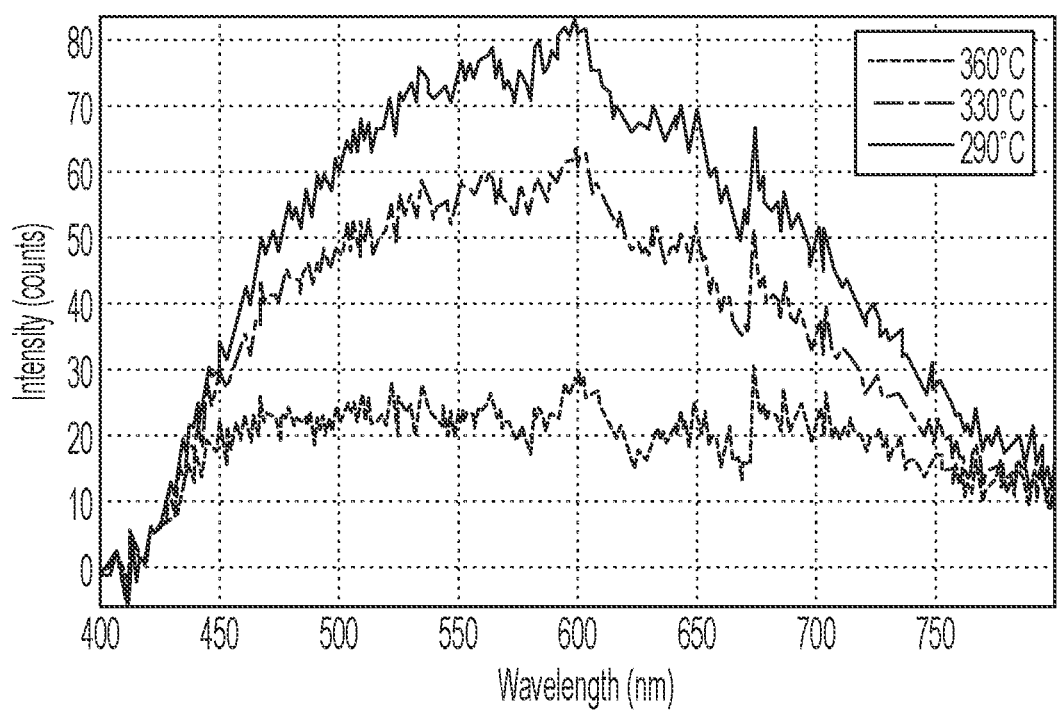
FIG. 3 graphically illustrates the mean intensity distribution of rock samples according to one or more embodiments described herein.
Figure 4:
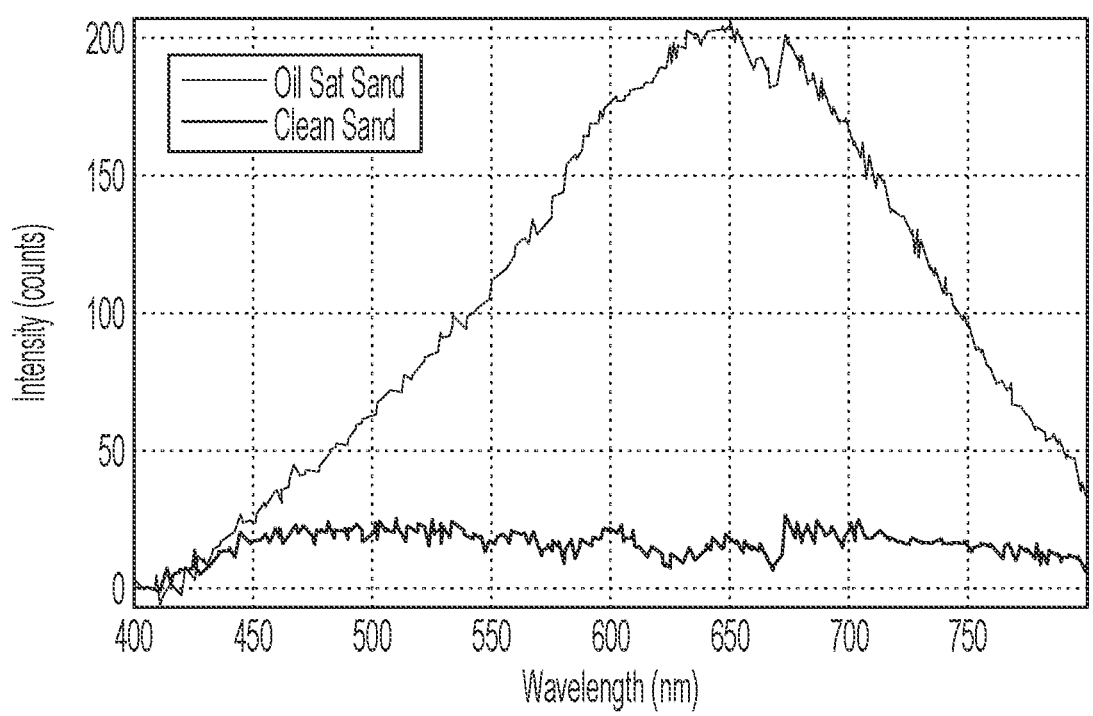
FIG. 4 graphically illustrates the mean intensity distribution of rock samples according to one or more embodiments described herein.

The mean intensity of a sequence of source rock samples in response to ultraviolet wavelengths (400 nm to 800 nm) was measured, as is shown in FIGS. 3 and 4. The ultraviolet light source was used to excite fluorescence in the samples and the intensity of the fluorescence was detected. The source rock samples were pure quartz sand. The source rock samples were artificially matured though pyrolysis experiments. There were 10 rock samples, where the first rock sample was artificially matured at 290° C., the second rock sample was artificially matured at 300° C., the third rock sample was artificially matured at 310° C., the fourth rock sample was artificially matured at 320° C., the fifth rock sample was artificially matured at 330° C., the sixth rock sample was artificially matured at 340° C., the seventh rock sample was artificially matured at 350° C., the eighth rock sample was artificially matured at 360° C., the ninth rock sample was clean sand, and the tenth rock sample was oil saturated quartz sand. Lithologically, the samples were identical and differences in the ultraviolet response are caused by kinetic changes during pyrolysis. The intensity of the first rock sample (artificially matured at 290° C.), the fifth rock sample (artificially matured at 330° C.), and the eighth rock sample (artificially matured at 360° C.) are shown in FIG. 3. The intensity of the ninth rock sample (clean sand) and the tenth rock sample (oil saturated sand) are shown in FIG. 4. A loss of fluorescence intensity was noted as the samples become more mature in both the spectral maps well as in the representative spectra. The fluorescence intensity (400-800 nm wavelengths) both visually and spectrally was seen to decrease with increasing maturity. The samples, although organic rich, were only weakly fluorescent. This is most likely attributable to the relatively low values of total organic carbon (TOC).

Figure 5:
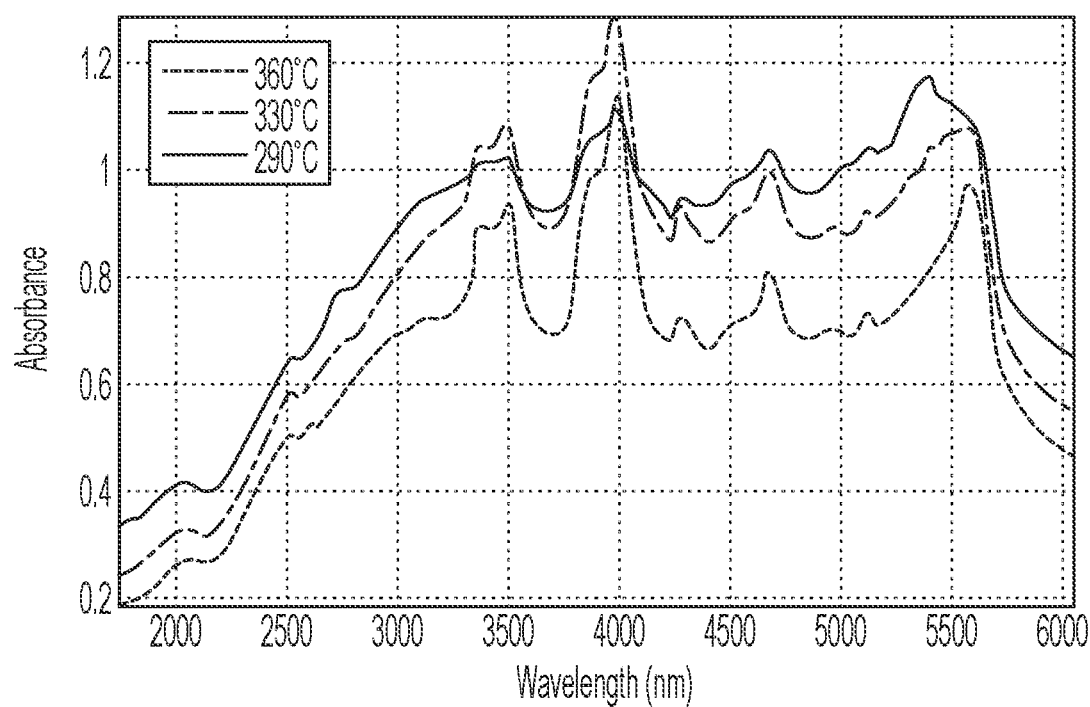
FIG. 5 graphically illustrates the mean absorbance distribution of rock samples according to one or more embodiments described herein.
Figure 6:
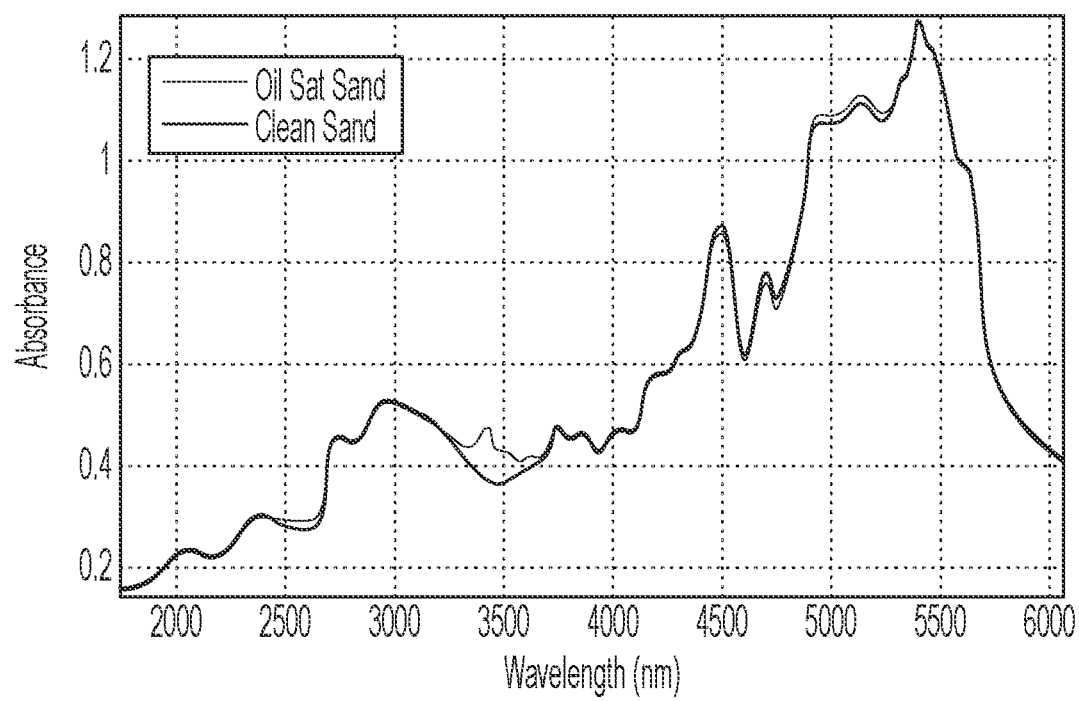
FIG. 6 graphically illustrates the mean absorbance distribution of rock samples according to one or more embodiments described herein.

The mean absorbance of a sequence of source rock samples in response to mid-wave infrared wavelengths (1750 nm to 6000 nm) was also measured, and is shown in FIGS. 5 and 6. These figures show source rock samples (i.e. organic rich carbonate mudstones) and pure quartz sand one clean and one treated with oil. In FIG. 5, the source rock samples were artificially matured though pyrolysis experiments. There were 10 rock samples, where the first rock sample was artificially matured at 290° C., the second rock sample was artificially matured at 300° C., the third rock sample was artificially matured at 310° C., the fourth rock sample was artificially matured at 320° C., the fifth rock sample was artificially matured at 330° C., the sixth rock sample was artificially matured at 340° C., the seventh rock sample was artificially matured at 350° C., the eighth rock sample was artificially matured at 360° C., the ninth rock sample was clean sand, and the tenth rock sample was oil saturated sand. The absorbance of the first rock sample (artificially matured at 290° C.), the fifth rock sample (artificially matured at 330° C.), and the eighth rock sample (artificially matured at 360° C.) are shown in FIG. 5. The absorbance of the ninth rock sample (clean sand) and the tenth rock sample (oil saturated sand) are shown in FIG. 6.

Figure 7:
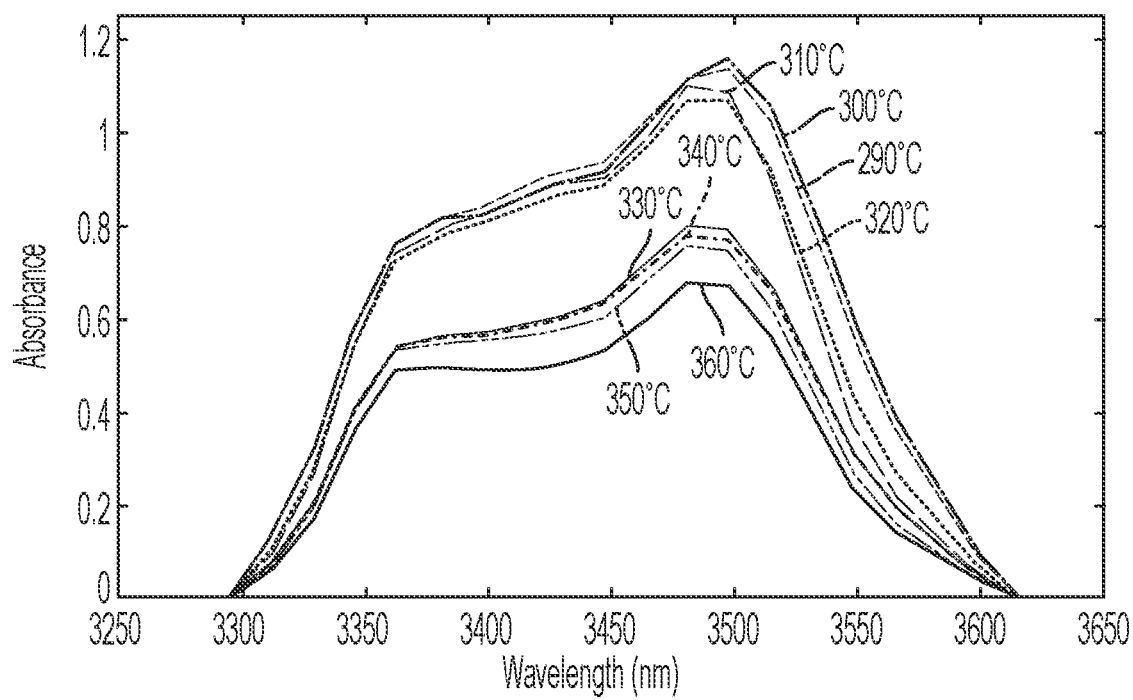
FIG. 7 graphically illustrates the mean absorbance distribution of rock samples according to one or more embodiments described herein.

Lithologically, the samples were identical and differences in the mid-wave infrared response are caused by kinetic changes during pyrolysis. The differences in the spectral maps between maturity end members (the first rock sample at 290° C. versus the eighth rock sample at 360° C.) were noted in the changes in the spectra shown in FIG. 5 specifically those between 3250 and 3650 nm. The maturity end members from immature (the first rock sample at 290° C.) to late oil (the eighth rock sample at 360° C.) each contain organic matter. However, the amount and composition of the organic molecules change with increasing maturity. When the spectra from FIG. 5 are linearly baseline corrected at anchor points of 3290 nm and 3620 nm, as well as normalized by the amount of total organic carbon (TOC) in the samples, the changes in the peaks between 3250-3600 nm show a clear trend with thermal maturity, as shown in FIG. 7. FIG. 7 clearly shows that as maturity increases, absorbance decreases. This reduction in absorbance is related to the conversion of the organic matter to liquid hydrocarbons as the samples are matured, leaving fewer aliphatic components in the residual organic matter. Therefore, this region of the spectrum may be used to identify TOC content (i.e. maturity/hydrocarbon presence).

FIG. 6 display the mean percent reflectance while the spectral data is in absorbance units, such that the brighter more reflective samples correspond to the spectra with lower absorbance values. While the individual spectra within the 3100 nm to 3750 nm range do correlate with hydrocarbon presence on the sand, they do not appear to correlate well with maturity. This occurs because of differences in the absorbance baseline for each sample, these differences may be due to a variety of factors including surface roughness and slightly different focal distances. To account for these differences, and to make quantitative comparisons among the samples, the spectra must be corrected to remove the effect of the varying baseline. This may be done in a similar manner as for FIGS. 5 and 7. After baseline correction, the absorbance or peak height of the clean sand vs. the oil saturated sand is compared, which is proportional to the abundance of hydrocarbons in the sample and maturity of the aged samples.

For the purposes of describing and defining the embodiments, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

As used herein, numerical value ranges include the endpoints unless otherwise expressly stated. Thus, for example, stating that "the wavelength may range from 450 to 550 nm" means that the wavelength may be 450 nm, may be 550 nm, or may be any integer between 450 and 550 nm.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

The invention claimed is:

1. A method of analyzing a geologic sample comprising:
illuminating the geologic sample with a light beam;
capturing an image of the geologic sample on a hyperspectral camera as a greyscale image, R-G-B color space image, or both, thereby collecting spectra reflected from a surface of the geologic sample, the spectra having varied wavelengths comprising mid-wave infrared wavelengths, ultraviolet wavelengths, or both;
processing the image to transform the image from the R-G-B color space image or greyscale image, or both, to Intensity, thereby transforming the spectra into a distribution of relative intensities of fluorescence or absorbance at the varied wavelengths; and
analyzing the Intensity to determine mineralogy, organic content, hydrocarbon presence, or combinations thereof of the geological sample by:
comparing the Intensity to a spectral library, the spectral library comprising previously recorded Intensities associated with specific mineralogy,
choosing a best match of the previously recorded Intensities to the Intensity,
determining the mineralogy of the geologic sample based on the mineralogy of the best match,
comparing the relative intensity in the wavelength range of 200 nm to 6000 nm of the Intensity to the best match,
observing differences in the relative intensity in the wavelength range of 200 nm to 6000 nm of the geologic sample versus the best match, the differences comprising changes in peak positions or magnitude of peaks within the Intensity, and
determining the organic content of the sample based on the differences, wherein the organic content is a qualitative assessment of the thermal maturity of the organic matter making up the organic content.

2. The method of claim 1, wherein capturing the image further comprises spatial line scanning.

3. The method of claim 1, further comprising cleaning the geologic sample prior to illuminating the geologic sample with the light beam.

4. The method of claim 3, wherein cleaning the geologic sample comprises flushing the geologic sample with a solvent.

5. The method of claim 1, further comprising capturing one or more additional images of the geologic sample from one or more additional surfaces.

6. The method of claim 1, wherein the hyperspectral camera comprises image sensor and a lens, and the geologic sample is positioned within a field of view of the camera.

7. The method of claim 1, wherein the hyperspectral camera comprises a pushbroom imaging spectral sensor.

8. The method of claim 1, wherein:
the mid-wave infrared wavelengths range from 2000 to 6000 nm;
the visible light wavelengths range from 400 to 1000 nm; and
the ultraviolet wavelengths range from 100 to 400 nm.

9. The method of claim 1, wherein analyzing the Intensity to determine mineralogy, organic content, hydrocarbon presence, or combinations thereof of the geological sample further comprises:
comparing the relative intensity in the wavelength range of 400 to 800 nm of the Intensity to the best match;
observing a second set of differences in the relative intensity in the wavelength range of 400 nm to 800 nm of the geologic sample versus the best match of the previously recorded Intensities, the second set of differences comprising changes in peak positions or magnitude of peaks within the Intensity; and
determining the hydrocarbon presence of the sample based on the second set of differences, wherein the hydrocarbon presence is a quantitative assessment of the presence and amount of hydrogen-carbon bonds present within the geologic sample.

10. The method of claim 1, further comprising:
drilling a wellbore;
acquiring the geologic sample from the wellbore; and
placing the geologic sample in a plate reader prior to illuminating the geologic sample with the light beam.

11. The method of claim 10, further comprising cleaning the geologic sample prior to illuminating the geologic sample with the light beam.

12. The method of claim 11, wherein cleaning the geologic sample comprises flushing the geologic sample with a solvent.

13. A method of analyzing a geologic sample comprising:
illuminating the geologic sample with a light beam;
capturing an image of the geologic sample on a hyperspectral camera as a greyscale image, R-G-B color space image, or both, thereby collecting spectra reflected from a surface of the geologic sample, the spectra having varied wavelengths comprising mid-wave infrared wavelengths, ultraviolet wavelengths, or both;
processing the image to transform the image from the R-G-B color space image or greyscale image, or both, to Intensity, thereby transforming the spectra into a distribution of relative intensities of fluorescence or absorbance at the varied wavelengths; and
analyzing the Intensity to determine mineralogy, organic content, hydrocarbon presence, or combinations thereof of the geological sample by:
comparing the Intensity to a spectral library, the spectral library comprising previously recorded Intensities associated with specific mineralogy,
choosing a best match of the previously recorded Intensities to the Intensity,
determining the mineralogy of the geologic sample based on the mineralogy of the best match,
comparing the relative intensity in the wavelength range of 400 nm to 800 nm of the Intensity to the best match,
observing differences in the relative intensity in the wavelength range of 400 nm to 800 nm of the geologic sample versus the best match, the differences comprising changes in peak positions or magnitude of peaks within the Intensity, and
determining the hydrocarbon presence of the sample based on the differences, wherein the hydrocarbon presence is a quantitative assessment of the presence and amount of hydrogen-carbon bonds present within the geologic sample.

14. The method of claim 13, wherein capturing the image further comprises spatial line scanning.

15. The method of claim 13, further comprising cleaning the geologic sample prior to illuminating the geologic sample with the light beam.

16. The method of claim 13, wherein cleaning the geologic sample comprises flushing the geologic sample with a solvent.

17. The method of claim 13, further comprising capturing one or more additional images of the geologic sample from one or more additional surfaces.

18. The method of claim 13, wherein the hyperspectral camera comprises image sensor and a lens, and the geologic sample is positioned within a field of view of the camera.

19. The method of claim 13, wherein the hyperspectral camera comprises a pushbroom imaging spectral sensor.

20. The method of claim 13, further comprising:
drilling a wellbore;
acquiring the geologic sample from the wellbore; and
placing the geologic sample in a plate reader prior to illuminating the geologic sample with the light beam.

\* \* \* \* \*